(12) United States Patent
Evans et al.

(10) Patent No.: US 10,398,841 B2
(45) Date of Patent: Sep. 3, 2019

(54) ADAPTER FOR A SYRINGE

(71) Applicant: West Pharmaceutical Services, Inc., Exton, PA (US)

(72) Inventors: Christopher Evans, Long Valley, NJ (US); Brian Costello, Whitehouse Station, NJ (US); Christopher Gieda, Long Valley, NJ (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 15/651,414

(22) Filed: Jul. 17, 2017

(65) Prior Publication Data

US 2017/0312436 A1 Nov. 2, 2017

Related U.S. Application Data

(60) Division of application No. 13/796,794, filed on Mar. 12, 2013, now Pat. No. 9,717,854, which is a continuation-in-part of application No. PCT/US2011/036251, filed on May 12, 2011.

(60) Provisional application No. 61/669,848, filed on Jul. 10, 2012.

(51) Int. Cl.
*A61M 5/31* (2006.01)
(52) U.S. Cl.
CPC ............ *A61M 5/31* (2013.01); *A61M 5/3137* (2013.01); *A61M 2005/3139* (2013.01)

(58) Field of Classification Search
CPC .... A61M 5/3137; A61M 5/31; A61M 5/3135; A61M 2005/3139; A61M 5/24
See application file for complete search history.

(56) References Cited

U.S. PATENT DOCUMENTS

| | | | |
|---|---|---|---|
| 1,589,969 | A | 6/1926 | Jaros |
| 3,076,455 | A | 2/1963 | McConnaughey |
| 4,540,405 | A | 9/1985 | Miller et al. |
| 4,687,472 | A | 8/1987 | Gross |
| 4,909,788 | A | 3/1990 | Egolf |
| 5,419,775 | A | 5/1995 | Haffner et al. |
| 5,496,286 | A | 3/1996 | Stiehl et al. |
| 5,509,903 | A | 4/1996 | Grendahl et al. |
| 5,984,901 | A | 11/1999 | Sudo et al. |

(Continued)

FOREIGN PATENT DOCUMENTS

| | | |
|---|---|---|
| CH | 403164 A | 11/1965 |
| DE | 29612079 U1 | 10/1996 |

(Continued)

*Primary Examiner* — Bhisma Mehta
*Assistant Examiner* — James D Ponton
(74) *Attorney, Agent, or Firm* — Panitch Schwarze Belisario & Nadel LLP

(57) ABSTRACT

An adapter for a syringe has a base portion having an insertion hole configured to surround and engage at least a portion of a barrel of the syringe. The base portion includes a top surface and an opposing bottom surface. At least one projection extends upwardly from the top surface of the base portion. At least one ramp portion is located proximate the at least one projection. A flange portion extends laterally outwardly from the base portion. The flange portion includes a top surface and an opposing bottom surface. The top surface of the base portion extends generally parallel to and is spaced between the top and bottom surfaces of the flange portion.

19 Claims, 13 Drawing Sheets

(56) References Cited

U.S. PATENT DOCUMENTS

| | | |
|---|---|---|
| 2003/0060777 A1 | 3/2003 | Benz et al. |
| 2003/0212380 A1* | 11/2003 | Barrelle ............... A61M 5/326 604/506 |
| 2007/0270763 A1 | 11/2007 | Tanner et al. |
| 2008/0097338 A1 | 4/2008 | Cheng |
| 2009/0062744 A1 | 3/2009 | Weilbacher et al. |
| 2009/0182284 A1* | 7/2009 | Morgan ............. A61M 5/3137 604/198 |
| 2009/0182285 A1 | 7/2009 | Lee et al. |
| 2011/0046604 A1 | 2/2011 | Felsovalyi et al. |
| 2012/0041388 A1 | 2/2012 | Blomquist |
| 2012/0279996 A1 | 11/2012 | Pappalardo et al. |
| 2013/0303993 A1 | 11/2013 | Evans et al. |

FOREIGN PATENT DOCUMENTS

| | | |
|---|---|---|
| EP | 0265876 A2 | 5/1988 |
| EP | 1285675 A1 | 2/2003 |

* cited by examiner

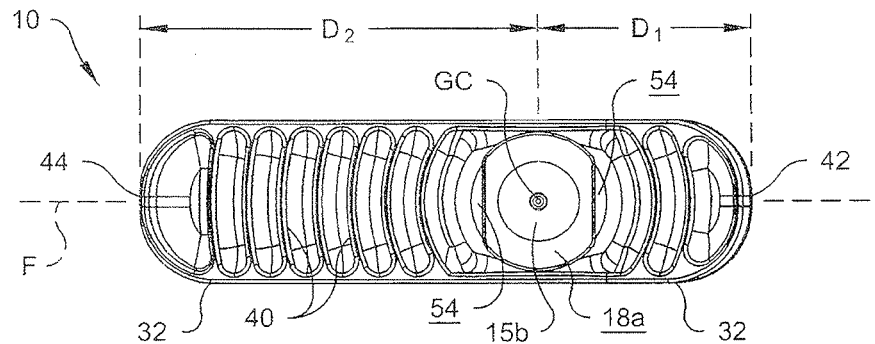
*Fig. 5A*
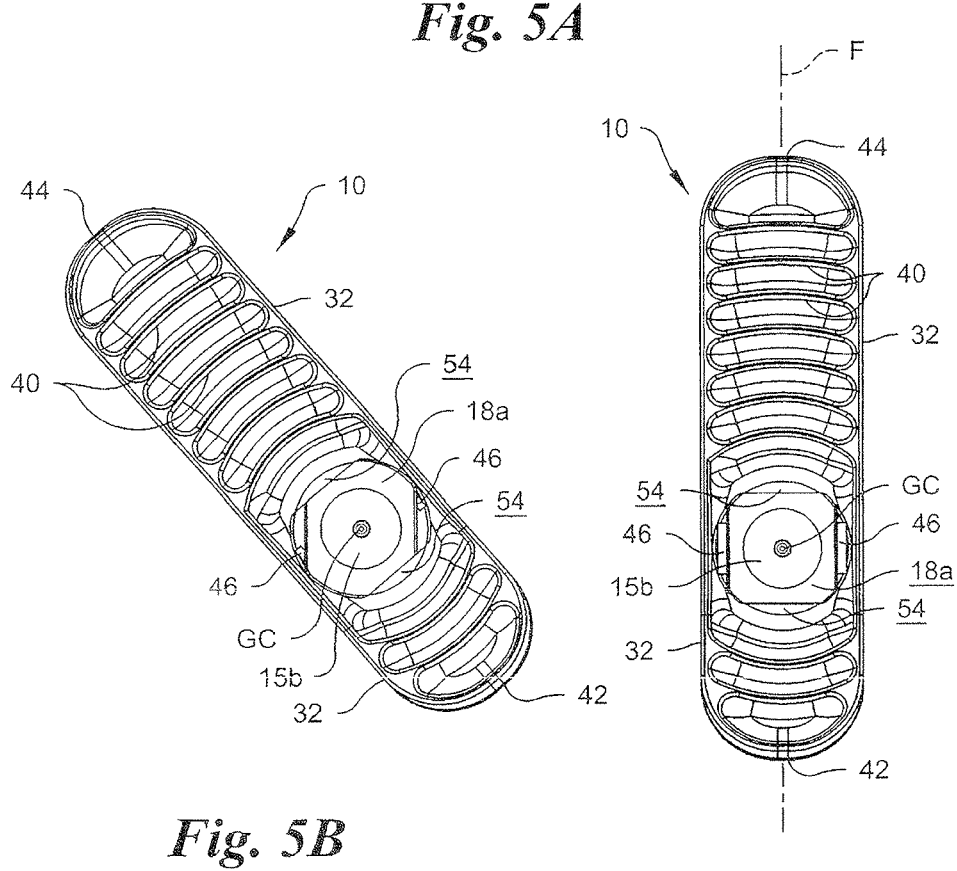
*Fig. 5B*
*Fig. 5C*

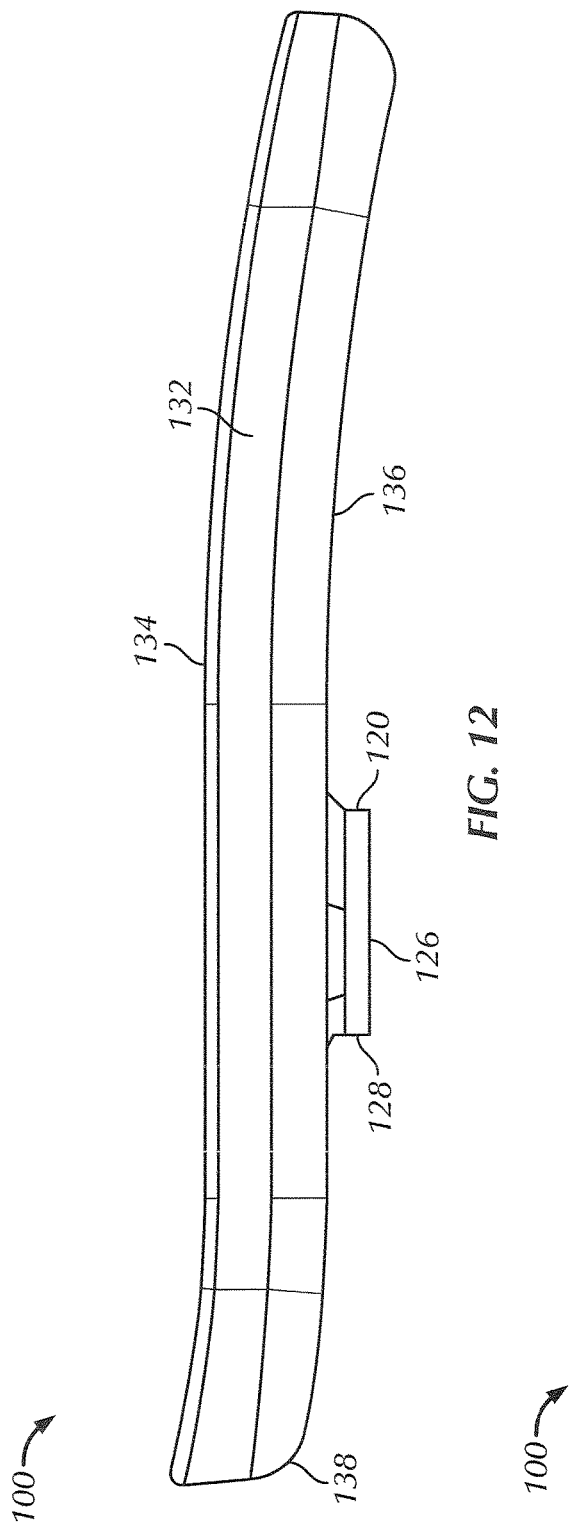
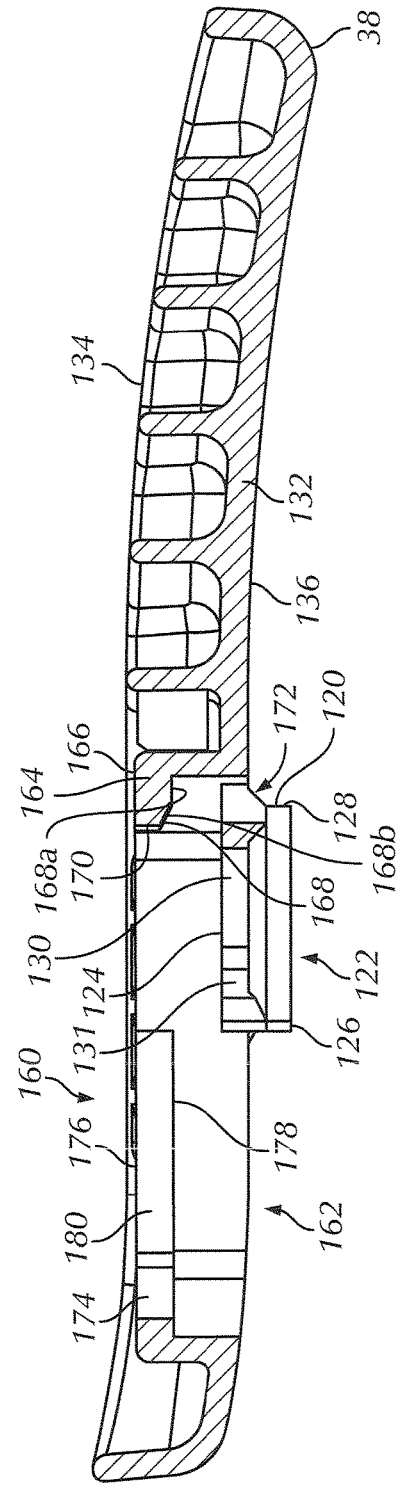

ADAPTER FOR A SYRINGE

CROSS-REFERENCE TO RELATED APPLICATIONS

This application is a divisional application of U.S. patent application Ser. No. 13/796,794 which is a continuation-in-part application of International Application No. PCT/US11/036251, filed May 12, 2011 and published in the English language on Nov. 15, 2012 under International Publication No. WO 2012/0154185 A1, and claims priority to U.S. Provisional Patent Application No. 61/669,848, filed Jul. 10, 2012, the disclosures of which are incorporated herein by reference in their entirety.

BACKGROUND OF THE INVENTION

The present invention relates generally to an accessory for a syringe and, more particularly, to an adapter removably installed onto a syringe, wherein the adapter is rotatable or slidable to lock onto a portion on the syringe.

A conventional syringe includes a barrel for holding medicament, a needle or cannula at a distal end thereof for injecting the medicament into a patient, and a small flange at a proximal end thereof. The flange is often referred to as a "finger flange," because the flange provides a surface or structure for which a healthcare professional's or other user's fingers grip or engage. The size, shape and overall configuration of the finger flange can have a direct effect on proper usability, leverage and control over the syringe. The finger flange on an International Organization for Standardization ("ISO") standard 1 milliliter, long syringe can be inadequate in size, shape and ergonomics.

Therefore, it would be desirable to create a device that eliminates or at least reduces the above-identified deficiencies of conventional finger flanges. For example, it would be desirable to create an accessory or an adapter that can be easily and preferably removably installed onto the finger flange of any syringe. It would also be desirable to create an accessory that may be locked onto the finger flange of a syringe by simply rotating the accessory. It would also be desirable to create an accessory that may be locked onto the finger flange of a syringe by simply linearly sliding the accessory with respect to the syringe. The present invention accomplishes the above objectives.

BRIEF SUMMARY OF THE INVENTION

Briefly stated, one aspect of the present invention is directed to an adapter for a syringe including a base portion having an insertion hole configured to surround and engage at least a portion of a barrel of the syringe. A flange portion extends laterally outwardly from the base portion. The flange portion includes a first distal end and an opposing second distal end. A longitudinal axis of the flange portion extends from the first distal end thereof to the opposing second distal end thereof. A first distance measured from a geometric center of the insertion hole to the first end of the flange portion is less than a second distance measured from the geometric center of the insertion hole to the second end of the flange portion. The first distance defines a first section of the flange portion and the second distance defines a second section of the flange portion. The first section has a cross-sectional shape that is one of at least slightly concave and at least slightly convex and the second section has a cross-sectional shape that is the other of at least slightly convex and at least slightly concave.

In another aspect, the present invention is directed to an adapter for a syringe including a base portion having an insertion hole configured to surround and engage at least a portion of a barrel of the syringe. The base portion includes a top surface and an opposing bottom surface. At least one projection extends upwardly from the top surface of the base portion. At least one ramped portion is located proximate to the at least one projection. A flange portion extends laterally outwardly from the base portion. The flange portion includes a top surface and an opposing bottom surface. The top surface of the base portion extends generally parallel to and is spaced between the top and bottom surfaces of the flange portion.

In yet another aspect, the present invention is directed to an adapter for a syringe including a base portion having a top surface, an opposing bottom surface and a passageway formed therethrough. The passageway is formed of a positioning hole and an insertion hole laterally adjacent thereto. The insertion hole is configured to surround and engage at least a portion of a barrel of the syringe. A flange portion extends laterally outwardly from the base portion. The flange portion includes a top surface and an opposing bottom surface. The top surface of the base portion extends generally parallel to and is spaced between the top and bottom surfaces of the flange portion.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 5A is a top plan view of the adapter and syringe shown in FIG. 4 in another configuration;

FIG. 5B is a top plan view of the adapter and syringe shown in FIG. 4 in yet another configuration;

FIG. 5C is a top plan view of the adapter and syringe shown in FIG. 4 in yet another configuration;

FIG. 12 is a side elevational view of the adapter shown in FIG. 7;

FIG. 13 is a cross-sectional elevational view thereof taken from line A-A of FIG. 10;

DETAILED DESCRIPTION OF THE INVENTION

Figure 1:
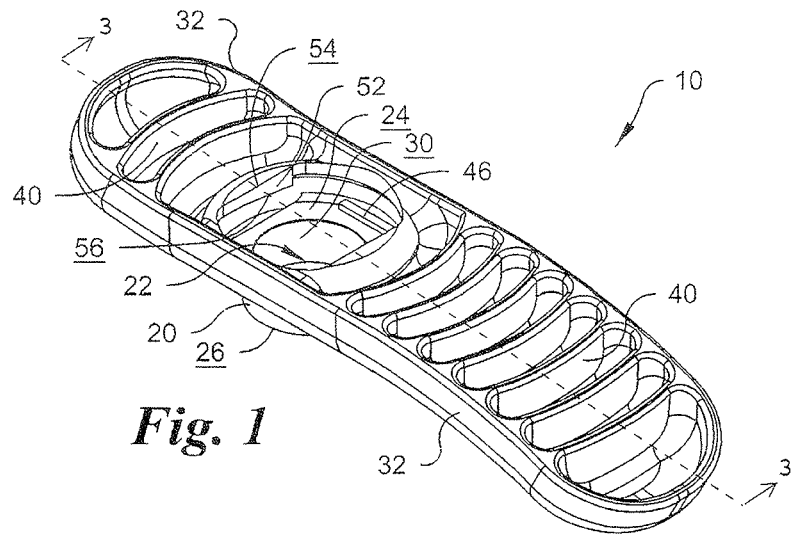
FIG. 1 is a perspective view of an adapter for a syringe according to a first preferred embodiment of the present invention.

Certain terminology is used in the following description for convenience only and is not limiting. The words "proximal," "distal," "upward," "bottom" and "top" designate directions in the drawings to which reference is made. The word "outwardly" refers to a direction away from the geometric center of the adapter or syringe, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Referring to the drawings in detail, wherein like numerals indicate like elements throughout the several views, FIGS. 1-6 show a first preferred embodiment of an accessory or adapter, generally designated 10, for a syringe, generally designated 12 (see FIGS. 4 and 6), and/or in combination with the syringe 12. The adapter 10 is preferably an accessory or separate component from the syringe 12, such that the adapter 10 can be easily installed onto at least a portion of the syringe 12 and/or is selectively removable therefrom. The adapter 10 provides a user with an ergonomic advantage, as compared to use of the syringe 12 without the adapter 10, while increasing the overall ease-of-use of the syringe 12. The adapter 10 may be installed onto the syringe 12 by a pharmacist, doctor and/or any other healthcare provider, or the adapter 10 may be installed by the consumer, patient or individual for self-injection.

As described in detail below, the adapter 10 of the first embodiment may be selectably locked or fixed onto at least a portion of the syringe 12 by twisting or rotating the adapter 10 with respect to the syringe 12.

Figure 4:
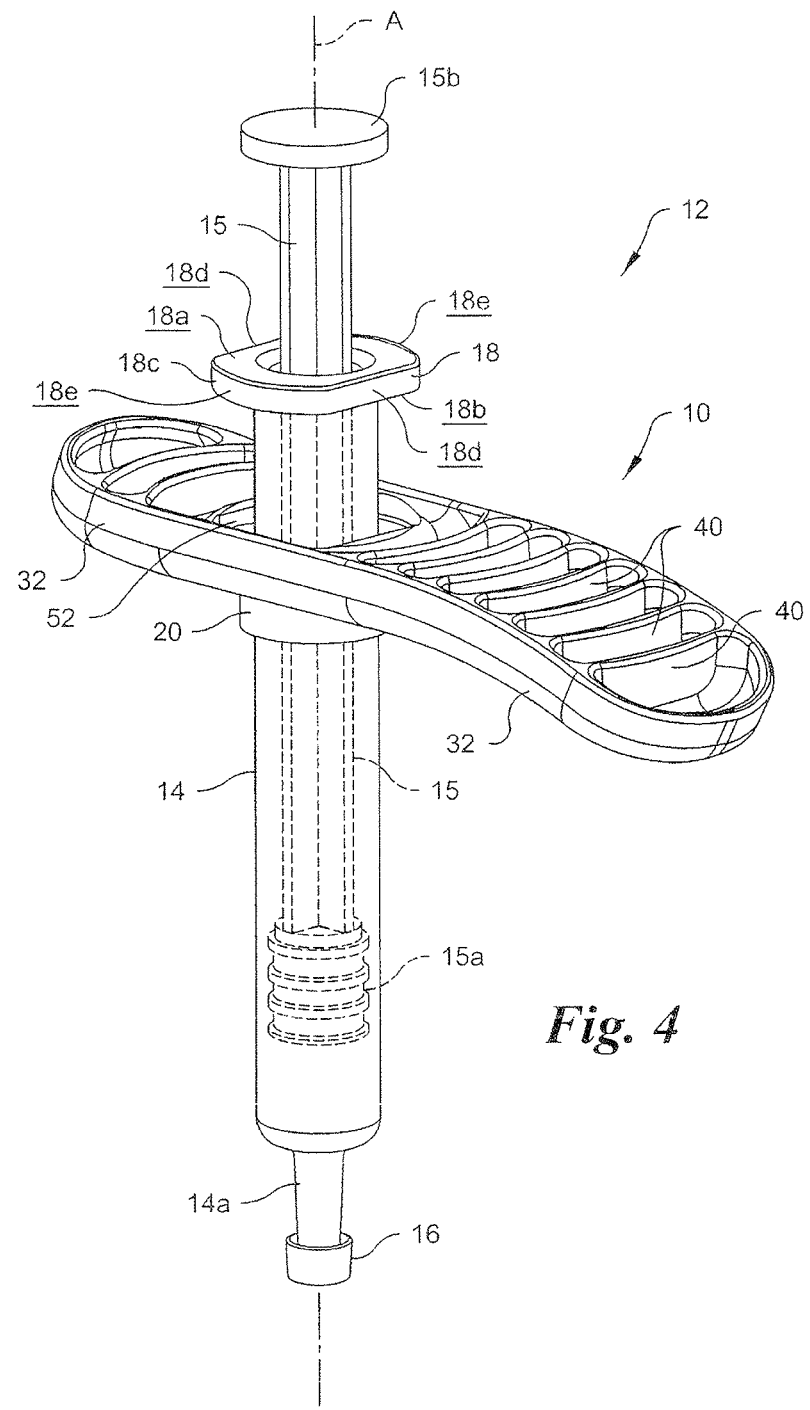
FIG. 4 is a perspective view of the adapter shown in FIG. 1 mounted to a syringe in a first configuration.
Figure 6:
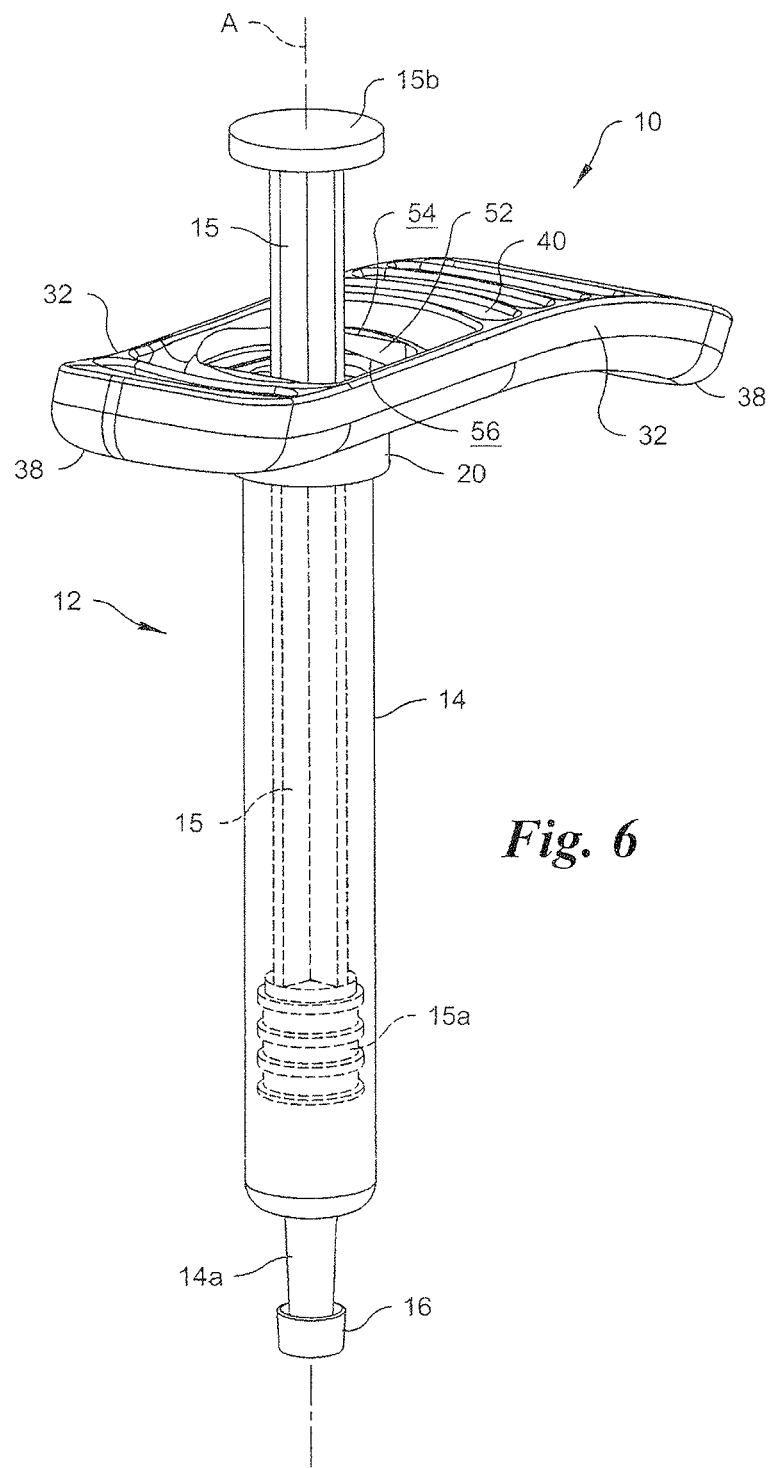
FIG. 6 is a perspective view of the adapter and syringe shown in FIG. 4 in yet another configuration.
Figure 7:
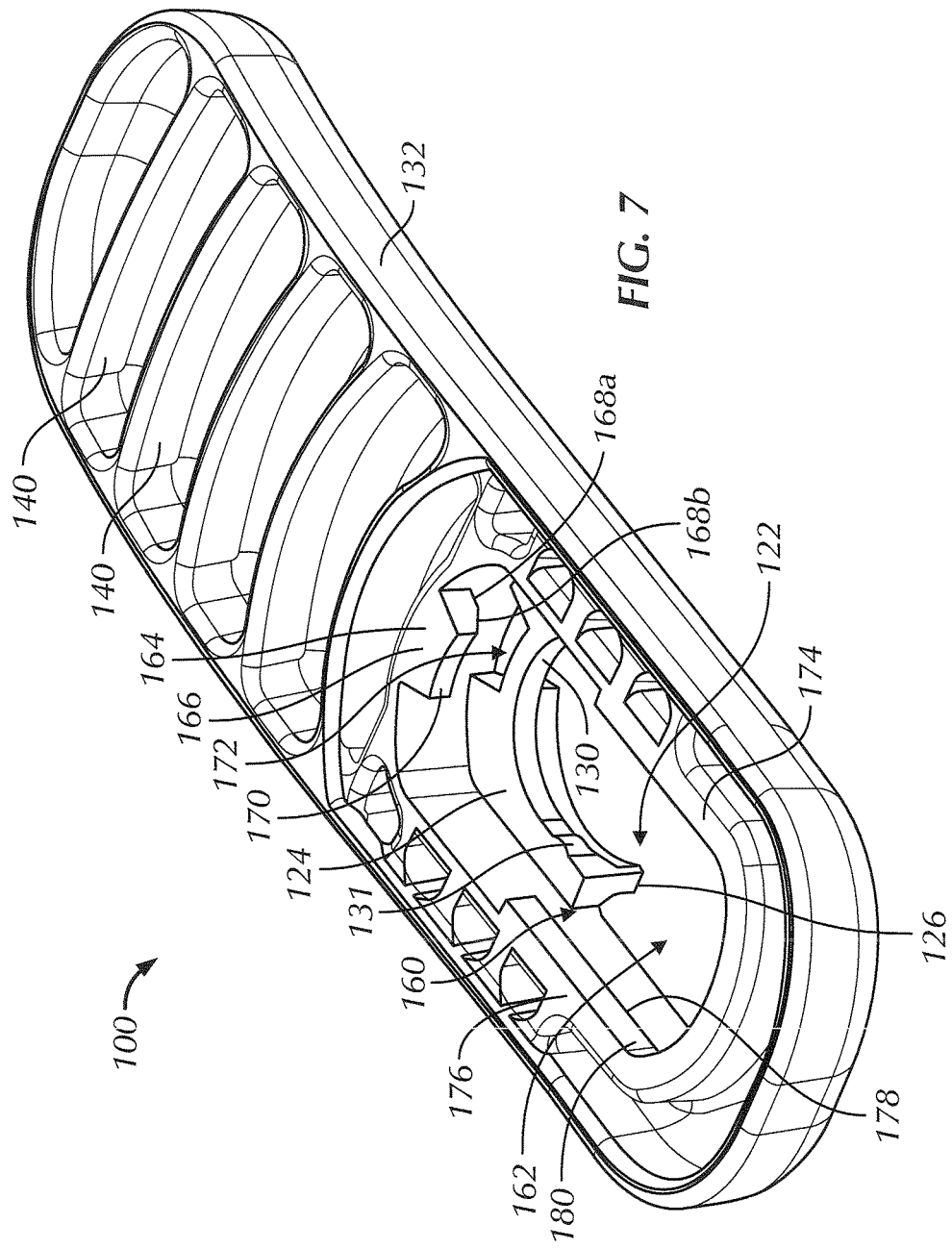
FIG. 7 is a top perspective view of an adapter for a syringe according to a second preferred embodiment of the present invention.
Figure 8:
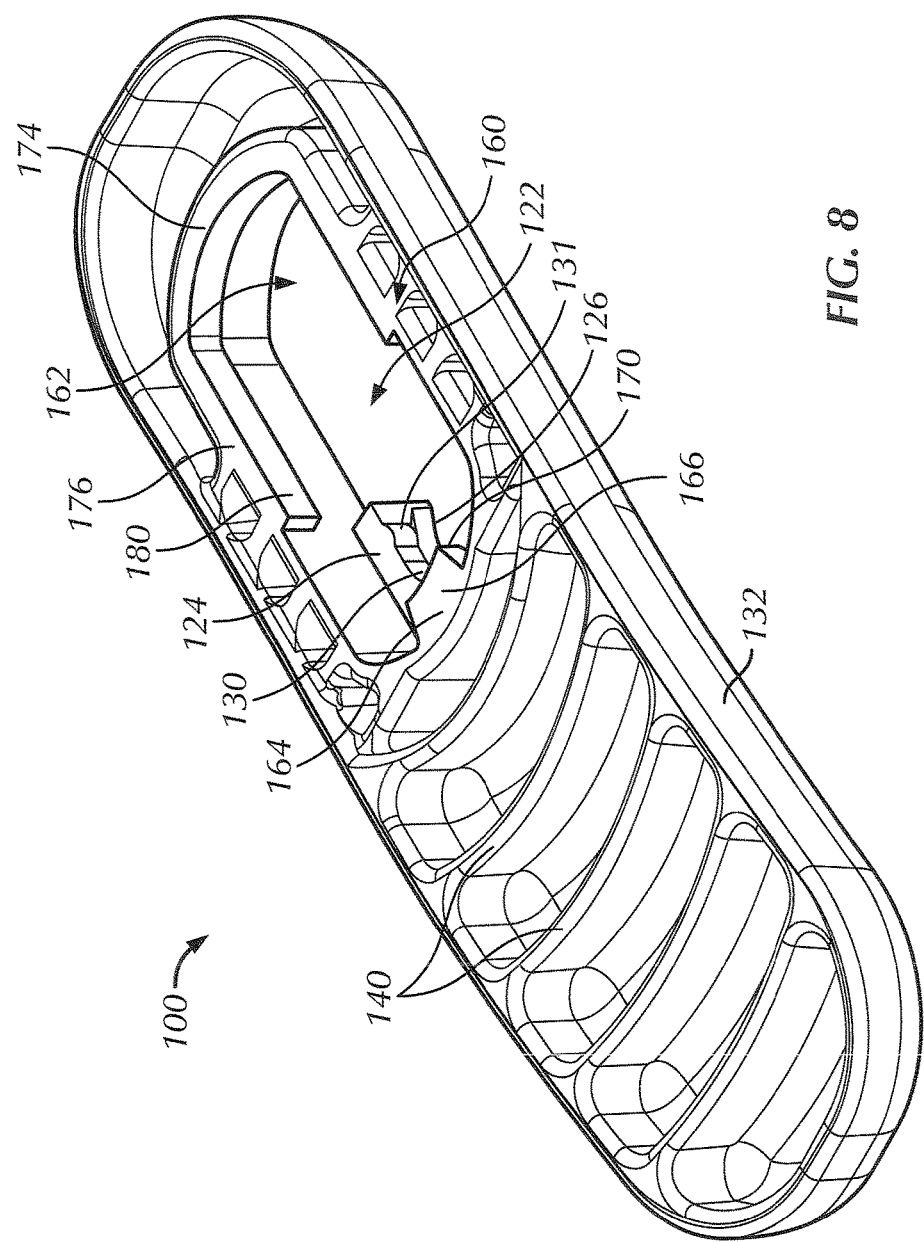
FIG. 8 is an enlarged top perspective view of the adapter shown in FIG. 7 taken from an alternative perspective.
Figure 9:
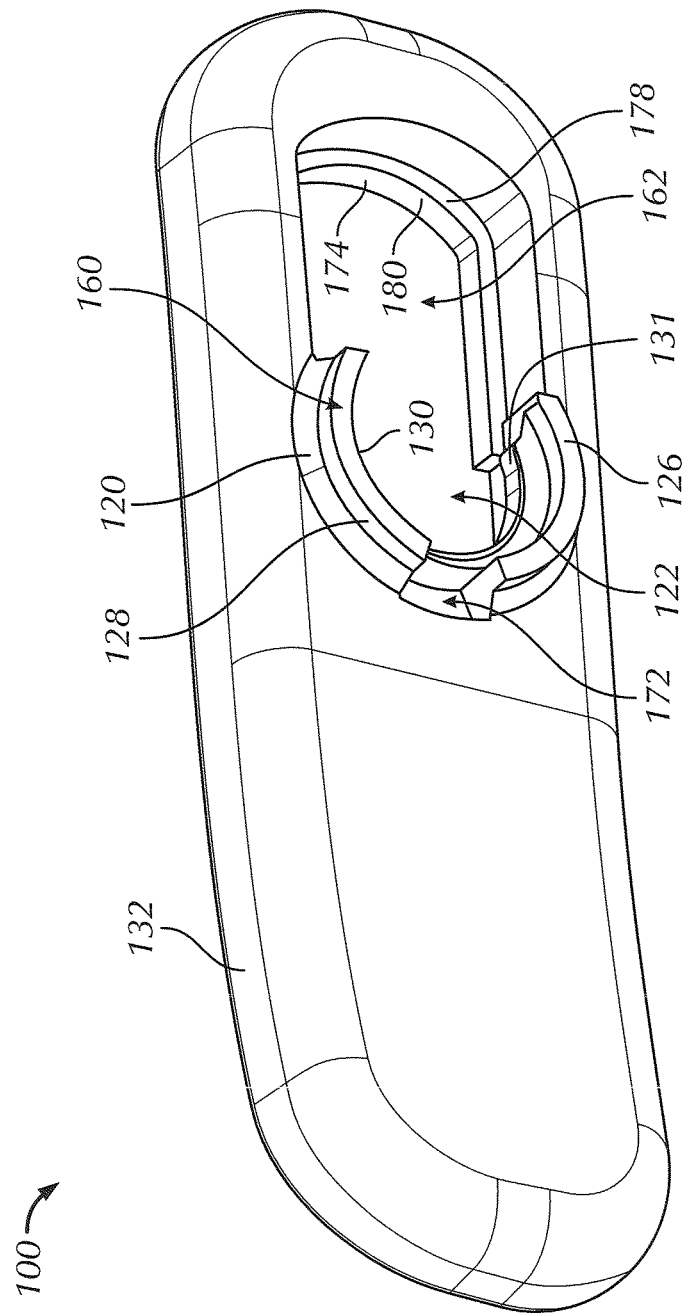
FIG. 9 is a bottom perspective view of the adapter shown in FIG. 7.
Figure 10:
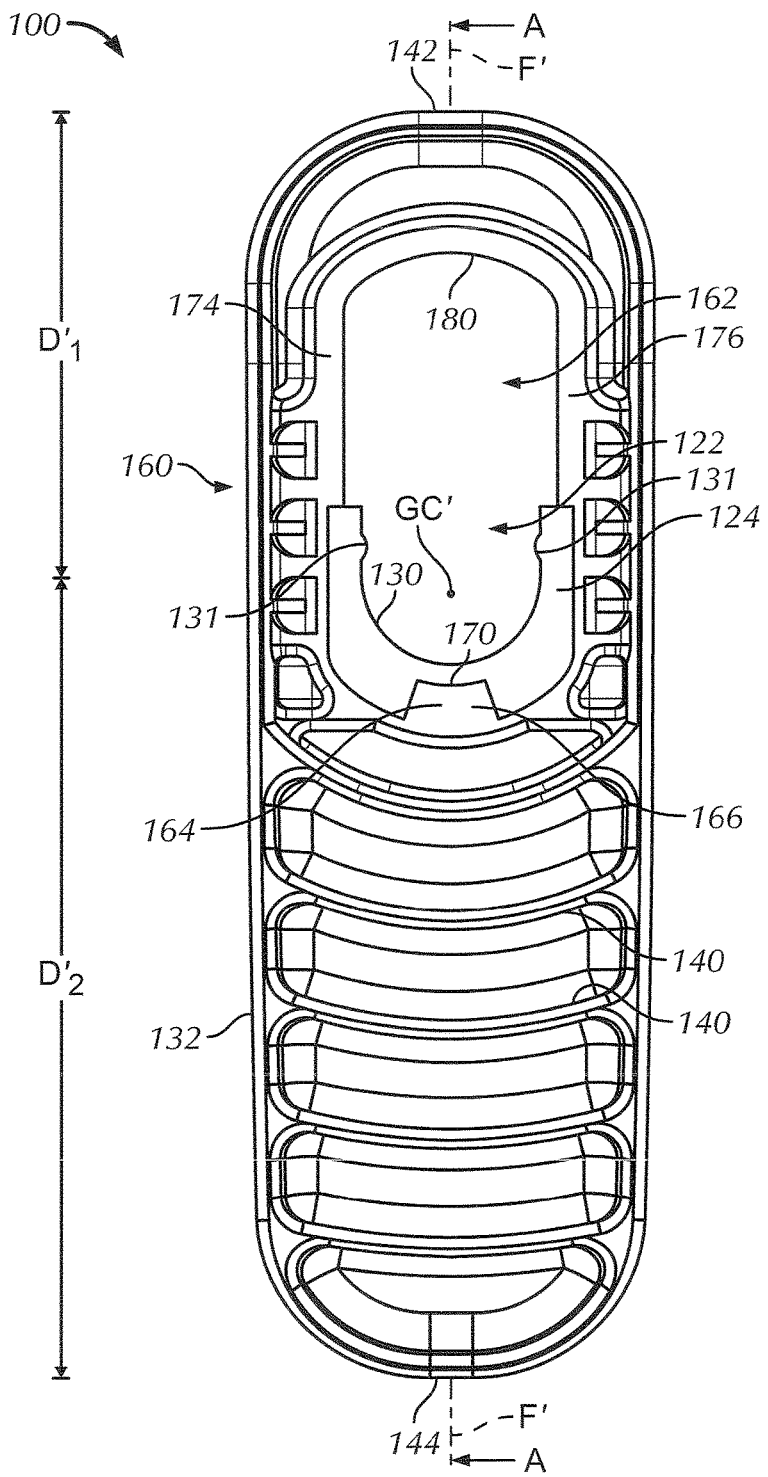
FIG. 10 is a top plan view of the adapter shown in FIG. 7.
Figure 11:
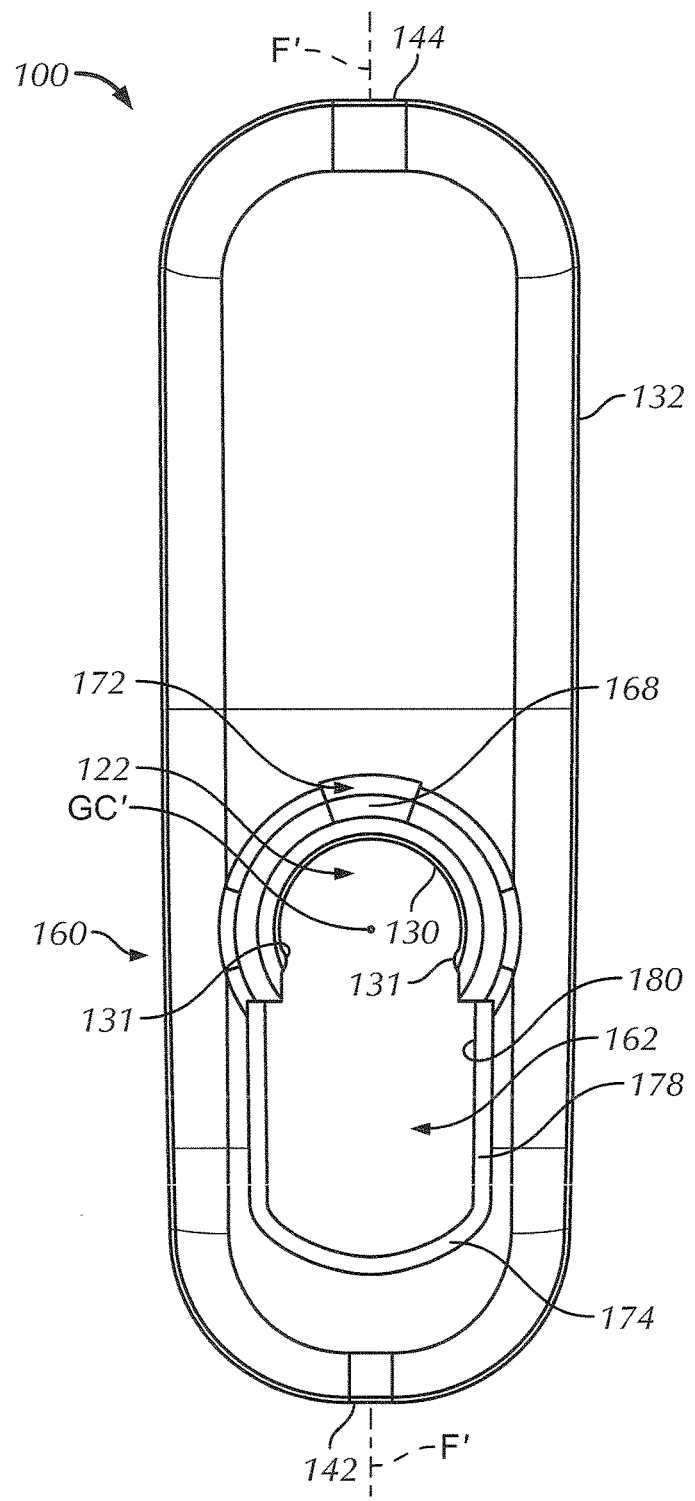
FIG. 11 is a bottom plan view of the adapter shown in FIG. 7.

Referring to FIGS. 4 and 6, the syringe 12 preferably includes a barrel 14 and a plunger 15 having a piston 15a (in phantom) and an opposing base 15b. The piston 15a is preferably slidable and sealingly engaged within a hollow cavity of the barrel 14. A needle or cannula (none shown) preferably extends outwardly from a distal end or hub 14a of the barrel 14. The hub 14a of the syringe 12 preferably includes an opening (not shown) that extends generally parallel to a longitudinal axis A of the syringe 12 for receiving and/or capturing a proximal end of the needle. A cap 16 may be removably attached to a distal end of a hub 14a if and/or when the needle is not attached to the hub 14a. The cap 16 is not a necessary component of the syringe 12, as the needle may be fixedly or non-removably mounted to the syringe 12. Alternatively, the cap 16 may be used to at least partially surround and/or engage at least a portion of the needle when the needle is attached to the hub 14a. Alternatively, the syringe 12 may be a Luer lock style syringe.

The barrel 14 of the syringe 12 may include two opposing planar surfaces and two opposing curved surfaces, each of which preferably extend generally the entire length of the barrel 14. Alternatively, the barrel 14 may have a generally cylindrical configuration in cross-section. The barrel 14 may be formed of glass, but the present invention is not so limited, as the barrel 14 may be formed of nearly any material, such as plastic or a polymer, capable of safely enclosing medicament or other substances. The hollow cavity of the barrel 14 preferably receives and holds medicament (none shown) therein. The medicament is preferably stored between a distal surface of the piston 15a and a proximal end or surface of the needle or cap 16. The syringe 12 is not limited to the inclusion of the barrel 14, the plunger 15, and the needle or cap 16, but maybe comprised of nearly any device that is able to contain medicament therein, be joined with the adapter 10, 100 and expel medicament therefrom, or otherwise inject medicament into the patient.

Referring again to FIGS. 4 and 6, a proximal end of the barrel 14 of the syringe 12 preferably includes a flange 18. At least a portion of the flange 18 extends generally, if not exactly, perpendicularly to the longitudinal axis A of the syringe 12. At least a portion of the flange 18 also preferably extends generally, if not exactly, parallel to a plane defined by the base 15b of the plunger 15 when the plunger 15 is properly positioned within the barrel 14. The flange 18 preferably includes a first, top or proximal surface 18a and an opposing second, bottom or distal surface 18b. Each surface 18a, 18b of the flange 18 is preferably generally flat or planar and defines a plane that extends generally, if not exactly, perpendicularly to the longitudinal axis A of the syringe 12. The surfaces 18a, 18b of the flange are preferably spaced-apart at a predetermined distance such that the flange 18 has a sidewall 18c therebetween. The sidewall 18c preferably defines a height of the flange 18. In one embodiment, the shape of the sidewall 18c of the flange 18 preferably matches or mirrors, at least in part, the shape of the exterior of the barrel 14 of the syringe 12. The sidewall 18c of the flange 18 may include two opposing planar surfaces 18d and two opposing curved surfaces 18e, such that the flange may form a "cut flange" (see FIG. 4). At least a portion of the flange 18 extends at least slightly radially outwardly beyond the radial outer surface of the barrel 14 at least at the curved surfaces 18e.

Figure 2:
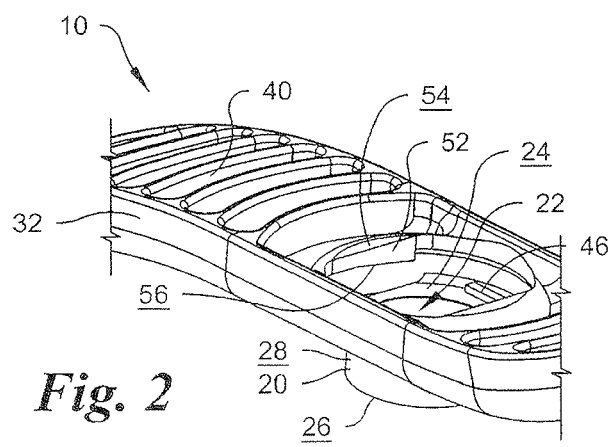
FIG. 2 is a perspective view of a portion of the adapter shown in FIG. 1 taken from an alternative perspective.
Figure 3:
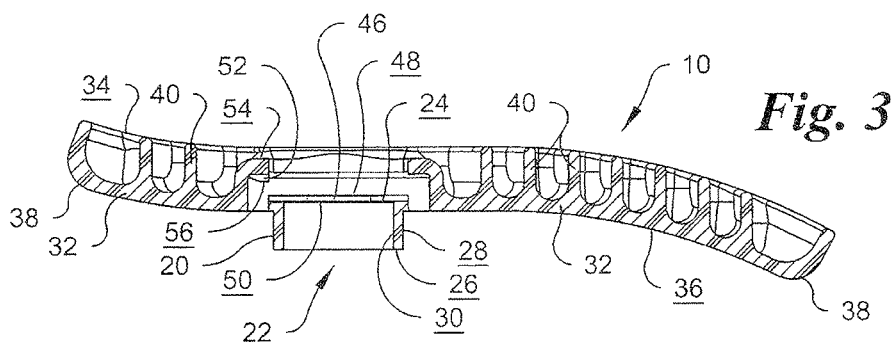
FIG. 3 is a cross-sectional elevation view of the adapter shown in FIG. 1 taken along line 3-3 of FIG. 1.

Referring now to FIGS. 1-4, the adapter 10 preferably includes a base portion 20 sized and shaped to receive at least a portion of the syringe 12 (e.g., the barrel 14) therethrough. The base portion 20 preferably extends at least outwardly from the remainder of the adapter 10. The base portion 20 of the adapter 10 of the first preferred embodiment preferably includes an insertion hole 22 configured to surround and engage at least a portion of the radial outer surface of the barrel 14 of the syringe 12. The insertion hole 22 preferably extends completely through the adapter 10. As shown in FIGS. 1-3, the base portion 20 preferably includes a first or top surface 24 and an opposing second or bottom surface 26. The base portion 20 also preferably includes an outer or exterior surface 28 and an opposing inner or interior surface 30. At least a portion of each of the exterior and interior surfaces 28, 30 are preferably circular in shape and match each other. Alternatively, the outer surface 28 and/or the inner surface 30 of the base portion 20 may generally match or mirror the two opposing planar surfaces 18d and two opposing curved surfaces 18e of the flange 18 and/or the barrel 14. However, the outer and inner surfaces 28, 30 of the base portion 20 are not limited to the above-described configuration, but may be formed in nearly any size and/or shape.

Referring to FIGS. 1-4, the adapter 10 preferably further includes a flange portion 32 that extends laterally outwardly from the base portion 20. When the adapter 10 is attached to the syringe 12, the flange portion 32 preferably extends outwardly from the barrel 14 of the syringe 12 generally perpendicularly to the longitudinal axis A of the syringe 12. The flange portion 32 preferably includes a first or top surface 34 and an opposing second or bottom surface 36. As shown in FIG. 3, the top surface 24 of the base portion 20 preferably extends generally parallel to and spaced between the top and bottom surfaces 34, 36 of the flange portion 32. The top and bottom surfaces 34, 36 of the flange portion 32 are each preferably nonlinear or curved linear in cross-sectional shape (see FIG. 3), such that one side of the flange portion 32 may be at least slightly convex (right side of FIG. 3) and another side of the flange portion 32 may be at least slightly concave (left side of FIG. 3). A peripheral edge 38 of the bottom surface of the 36 of the flange portion 32 is preferably arcuate or concave in shape. The peripheral edge 38 preferably extends around the entire perimeter or periphery of the flange portion 32. The flange portion 32 may be formed of a polymeric or metallic material, but the flange portion 32 may be formed of any light weight, high strength material that allows for the functionality described herein.

Referring to FIGS. 1, 3, 5A and 5C, a longitudinal axis F of the flange portion 32 of the adapter 10 of the first preferred embodiment preferably extends from a first distal or outer-most end 42 thereof to an opposing second distal or outer-most end 44 thereof. It is preferred that a first distance $D_1$ measured from a geometric center GC of the insertion hole 22 to the first distal end 42 of the flange portion 32 is less than a second distance $D_2$ measured from the geometric center GC of the insertion hole 22 to the second distal end 44 of the flange portion 32. However, the adapter 10 is not limited to the above-described configuration as the first and second distances may be of any size ratio. At least one and preferably a plurality of laterally spaced-apart ribs 40 extend downwardly from the top surface 34 of the flange portion 32. As shown in FIG. 5A, each rib 40 preferably extends generally perpendicularly to the longitudinal axis F of the flange portion 32. The ribs 40 may be at least slightly concave in shape with respect to the geometric center GC of the insertion hole 22. The ribs 40 provide structural rigidity to the adapter 10 and provide a gripping surface for the user, particularly for the thumb of the user.

As described in detail below, the structure of the adapter 10 of the first preferred embodiment allows the adapter 10 to be selectively fixed and/or locked onto at least a portion of the barrel 14, such as the flange 18, of the syringe 12. Initially, it is preferred that the adapter 10 is moved or slid along the barrel 14 until at least a portion of the adapter 10 contacts and/or engages the flange 18. Then, it is preferred that the adapter 10 is twisted or rotated in a first rotational direction (i.e., clockwise) with respect to the syringe 12. To accomplish the above result, the adapter 10 preferably includes at least one projection 46 that extends upwardly from the top surface 24 of the base portion 20. The projection 46 shown in FIGS. 1-3, 5B and 5C is generally rectangular in shape and extends generally, if not exactly, parallel to the longitudinal axis F of the flange portion 32. In one embodiment, as shown in FIG. 3, a top surface 48 of the projection 46 extends a predetermined distance above the top surface 24 of the base portion 20, and a bottom surface 50 of the projection 46 is positioned at and/or formed unitarily and integrally with the top surface 24 of a base portion 20. However, the projection 46 is not limited to the above-described size, shape and/or configuration, but may be any size-shape or configuration that allows for the functionality described therein.

As shown in FIGS. 1-3, the adapter 10 of the first preferred embodiment preferably includes at least one ramp portion 52 located proximate to the at least one projection 46. The ramp portion 52 preferably includes a first or top surface 54 and an opposing second or bottom surface 56. The top surface 54 of the ramp portion 52 is preferably at least generally flat or planar and may extend generally coplanar with the top surface 34 of the flange portion 32 or slightly below the top surface 34 of the flange portion 32 (see FIG. 3). At least a portion of the bottom surface 56 of the ramp portion 52 is also preferably at least generally flat or planar. However, at least a portion of the bottom surface 56 of the ramp portion 52 preferably extends at an angle with respect to the top surface 54 thereof. It is preferred that at least a portion of the bottom surface 56 of the ramp portion 52 extends at an angle of approximately 5 to 45 degrees, and more particularly about 30 degrees, with respect to a plane defined by the top surface 54 of the ramp portion 52.

In the first preferred embodiment, as shown in FIGS. 5A-5C, the adapter 10 includes two spaced-apart projections 46 and two spaced-apart ramp portions 52. As shown in FIG. 5C, it is preferred that the two projections 46 are separated by the longitudinal axis F of the flange portion 32, and that each of the ramp portions 52 are bisected by the longitudinal axis F of the flange portion 32. However, the projections 46 and ramp portions 52 are not limited to the above-described positioning and/or configuration. As described in more detail below, the above-described structure and configuration allows for the flange 18 of the syringe 12 to be rotated between and held or locked in place by at least one of the projections 46 and at least one of the ramp portions 52, and more preferably by the two projections 46 and two ramp portions 52.

A method of attaching the adapter 10 of the first preferred embodiment to the syringe 12 of the present invention preferably includes inserting the distal end of the barrel 14 of the syringe 12 into the insertion hole 22 of the adapter 10 through the top surface 24 of the base portion 20 first. It is preferred that the adapter 10 is moved with respect to the syringe 12 or slid along the barrel 14 toward the flange 18 of the syringe 12 until the top surface 24 of the base portion 20 contacts and/or engages the bottom surface 18b of the flange 18 of syringe 12. It is preferred that the adapter 10 is twisted or rotated with respect to the syringe 12 to generally fix or lock the adapter 10 onto the flange 18 of the syringe 12. It is also preferred that the adapter 10 is rotated approximately 90 degrees with respect to the syringe 12 generally lock the adapter 10 onto the syringe 12.

FIGS. 4-6 show the progression of attaching and/or locking the adapter 10 of the first embodiment to the syringe 12. After the syringe 12 is inserted into the insertion hole 22 of the adapter 10 or the adapter 10 is slid over the barrel 14 on the syringe 12 (see FIG. 4) until the bottom surface 18b of the flange 18 engages the top surface 24 of the base portion 20, the flange 18 is positioned with respect to the adapter 10 as shown in FIG. 5A. It is preferred that one of the adapter 10 and syringe 12 is held stationery while the other is rotated, such that at least a portion of the flange 18 begins to move beneath the ramp portions 52, the top surfaces 54 of which are shown in FIG. 5B. Continued rotation or twisting of one of the adapter 10 and syringe 12 with respect to the other occurs until the flange 18 is position with respect to the adapter 10 such that the two opposing planar surfaces 18d of the flange extend generally parallel to the two projections 46, as shown in FIG. 5C. In the configuration shown in FIG. 5C, opposing portions of the flange 18 are positioned between the bottom surface 56 of each ramp portion 52 and a portion of the top surface 24 of the base portion 20. This configuration generally locks the adapter 10 onto the syringe 12.

The angled configuration of at least a portion of the bottom surface 56 of each ramp portion 52 generally requires a twisting or rotating force of increasing magnitude as the flange 18 is locked within the adapter 10, as shown in FIG. 5C. It is preferred that an audible or tactile sound or click is generated once the flange 18 is positioned with respect to the adapter 10 as shown in FIG. 5C, so as to alert the user that the adapter 10 is in a final locked configuration. Once the adapter 10 is in the final locked configuration, the syringe 12 may be used as is conventional in the art (see FIG. 6).

Referring to FIGS. 7-16, there is shown a second preferred embodiment of an accessory or adapter, generally designated 100, for a syringe, generally designated 12 (see FIGS. 14-16), and/or in combination with the syringe 12. The reference numerals of the second preferred embodiment are distinguishable from those of the first preferred embodiment by an addition of one-hundred (100) or a prime (') symbol, but otherwise indicate the same or similar elements as indicated in the first preferred embodiment, except as otherwise specified. At least certain components of the base portion 120 of the second preferred embodiment are substantially similar to those of the first preferred embodiment described above. Also, the overall shape of the flange portion 132 of the second preferred embodiment is substantially similar to that of the first preferred embodiment described above (see FIGS. 7-10). The description of certain similarities between the embodiments may be omitted herein for the sake of brevity and convenience, and, therefore, is not limiting. Also, the same syringe 12 described above, or one substantially thereto, is used with the adapter 100 of the second preferred embodiment.

Referring to FIGS. 7-16, a distinguishing feature of the second preferred embodiment is that the adapter 100 may be selectably locked or fixed onto at least a portion of the syringe 12 by linearly sliding the adapter 100 with respect to the syringe 12. That is, relative rotation between the syringe 12 and the adapter 100 is not required to lock the two together, which may be beneficial for individuals with rheumatoid arthritis (RA) or any other ailment or disability.

Referring now to FIGS. 7, 9 and 11-16, the base portion 120 of the adapter 100 of the second preferred embodiment preferably surrounds, defines and/or is aligned with the insertion hole 122. At least a portion of the interior surface 130 is preferably curved or arcuate and at least slightly larger than an outer periphery of the barrel 14 of the syringe 12, so that at least a portion of the barrel 14 can fit therein. However, the outer and inner surfaces 128, 130 of the base portion 120 are not limited to the above-described configuration, but may be formed in nearly any size and/or shape.

Referring now to FIGS. 7-11 and 13-16, a passageway 160 preferably extends completely through the adapter 100. The passageway 160 has a generally ovular shape when viewed from above and/or below (see FIGS. 10-11). The passageway 160 is preferably comprised of an insertion hole 122 laterally adjacent to a positioning or sliding hole 162. In other words, it is preferred that the combination of the insertion hole 122 and the sliding hole 162 form the passageway 160. As described in detail below, the insertion hole 122 has a size, shape and/or configuration that is distinct from that of the sliding hole 162. The insertion hole 122 is preferably sized and/or shaped, or includes specific features as described in detail below, such that the adapter 100 can lock onto or engage at least a portion of the syringe 12, such as the flange 18 (shown in phantom in FIGS. 14-16), when the syringe 12 is inserted into the insertion hole 122 at the proper orientation.

As shown in FIGS. 7-11 and 13, at least one and preferably two diametrically opposed tabs 131 extend at least slightly inwardly from the interior surface 130 of the base portion 120 and into or toward the insertion hole 122. Each tab 131 is at least partially curved or arcuate in shape. As described in detail below, each tab 131 preferably engages at least a portion of the exterior surface of barrel 14 of the syringe 12 when the adapter 100 is locked and/or secured to the syringe 12. Preferably, the tabs 131 may at least slightly flex away from each other so as to accommodate the barrel 14 of the syringe 12 therebetween and engage the barrel 14 in an interference fit. The tabs 131 preferably provide a separate and additional point of contact between the adapter 10 and the syringe 12 to lock the adapter 100 onto the syringe 12.

As shown in FIGS. 7-8, 10 and 13-15, at least one projection 164 preferably extends at least slightly radially inwardly from the flange portion 132 and into the passageway 160. The projection 164 is preferably positioned on a side of the insertion hole 122 generally away from or opposite to the sliding hole 162. The projection 164 preferably includes a first or top surface 166, an opposing second or bottom surface 168, and an interior surface 170 extending from the top surface 166 to the bottom surface 168. The top surface 166 of the projection 164 is preferably flat and extends generally coplanar with at least a portion of the top surface 134 of the flange portion 132. At least a first portion 168a of the bottom surface 168 is preferably flat, and at least a second portion 168b of the bottom surface 168 is preferably chamfered to be at least slightly arcuate or slanted. It is preferred that the second portion 168b of the bottom surface 168 extends at an angle of approximately 5 to 45 degrees, and more particularly about 30 degrees, with respect to a plane defined by the top surface 166 of the projection 164. The second portion 168b of the bottom surface 168 preferably connects the interior surface 170 to the first portion 168a of the bottom surface 168. At least a portion of the interior surface 170 of the projection 164 is at least slightly curved or arcuate. An aperture 172 is preferably vertically aligned with and has a periphery that is preferably at least slightly larger than that of the projection 164. The aperture 172 allows for the projection 164 to be molded.

Referring to FIGS. 7-11 and 13-16, at least one ledge 174 preferably extends at least slightly radially inwardly from around at least a portion of the sliding hole 162 of the adapter 100. The ledge 174 preferably includes a first or top surface 176, an opposing second or bottom surface 178, and an interior surface 180 extending from the top surface 176 to the bottom surface 178. The top surface 176 of the ledge 174 is preferably flat and extends generally coplanar with at least a portion of the top surface 134 of the flange portion 132 and/or at least a portion of the top surface 166 of the projection 164. The bottom surface 178 of the ledge 174 is also preferably flat and is preferably positioned vertically above the top surface 124 of the base portion 120 (see FIG. 13). The ledge 174 preferably prevents the syringe 12 from moving completely through the sliding hole 162 of the adapter 100. In particular, if a user attempts to pass the entire syringe 12 through the sliding hole 162 of the adapter 100, the ledge 174 contacts or engages at least a portion of the flange 18 of the syringe 12, thereby preventing the entire syringe 12 from passing through the sliding hole 162 of the adapter 100. In addition, the ledge 174 preferably prevents the syringe 12 from being inserted downwardly into the sliding hole 162 of the adapter 100 from above (i.e., proximate the top surface 134 of the flange portion 132). In particular, if a user attempts to insert the syringe 12 downwardly through the sliding hole 162 of the adapter 100 from above, the ledge 174 would preferably contact or engage at least a portion of the flange 18 of the syringe 12, thereby preventing the syringe 12 from being inserted entirely through the sliding hole 162 of the adapter 100 from above.

As described in detail below, the adapter 100 of the second preferred embodiment is capable of being selectively fixed and/or locked onto at least a portion of the barrel 14, such as the flange 18, of the syringe 12. Initially, it is preferred that a geometric center of the sliding hole 162 of the adapter 100 is generally aligned with the longitudinal axis A of the syringe 12. At least a proximal portion of the syringe 12, such as the base 15b of the plunger 15, is preferably inserted upwardly into the sliding hole 162 of the adapter 100 from below (i.e., proximate the bottom surface 136 of the flange portion 132). The syringe 12 is preferably inserted upwardly into the sliding hole 162 preferably until the flange 18 is generally aligned with the base portion 120 of the adapter 100. More specifically, the syringe 12 is preferably inserted upwardly into the sliding hole 162 until the bottom surface 18b of the flange 18 of the syringe 12 is generally aligned with or at least slightly above (i.e., with respect to the longitudinal axis A) the top surface 124 of the base portion 120. The syringe 12 is preferably prevented from being inserted further into the sliding hole 162 due to contact between at least a portion of the bottom surface 178 of the ledge 174 of the adapter 100 and at least a top surface 18a of the flange 18 of the syringe 12.

Figure 14:
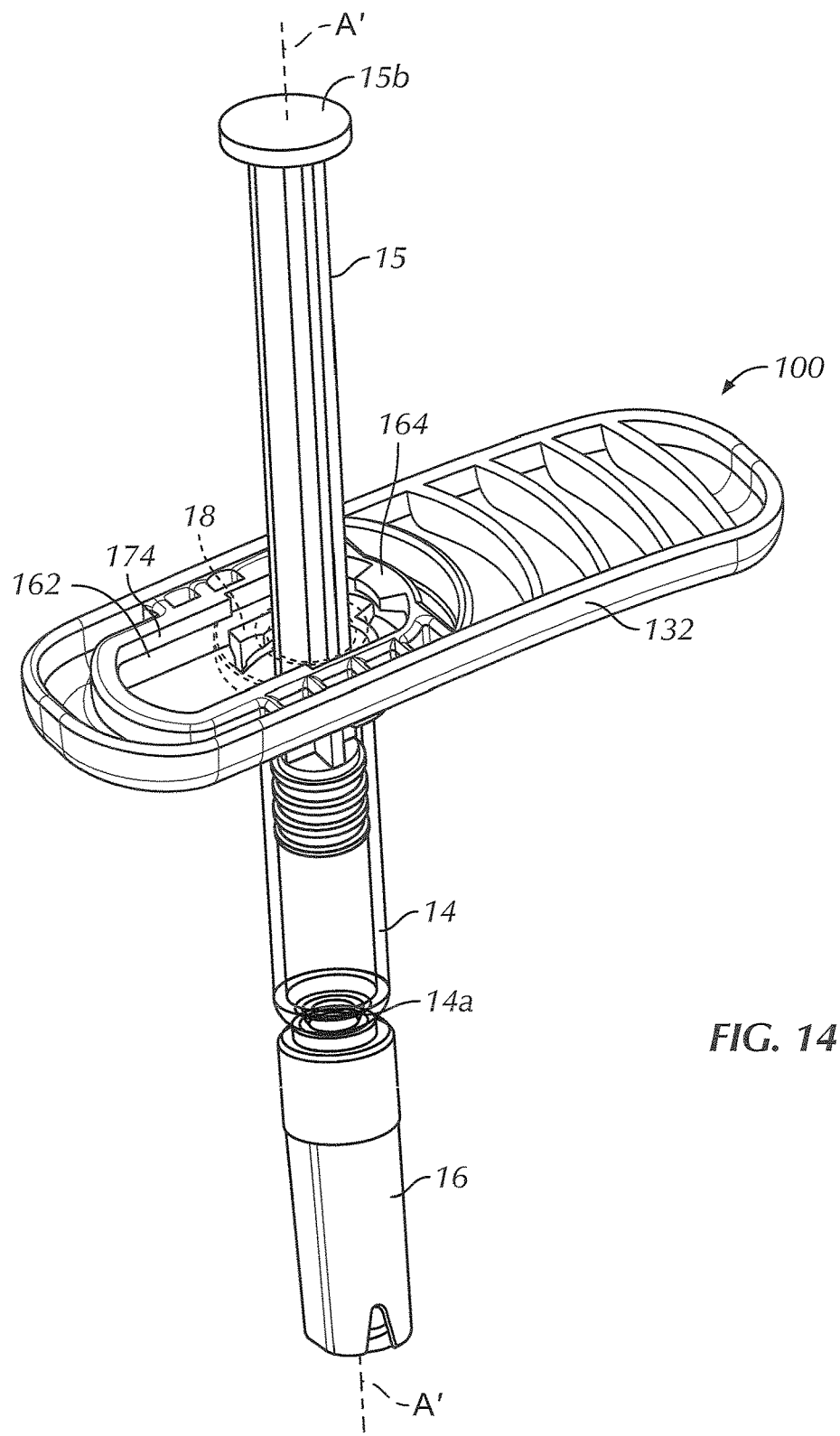
FIG. 14 is a top perspective view of the adapter shown in FIG. 7 mounted to a syringe.
Figure 15:
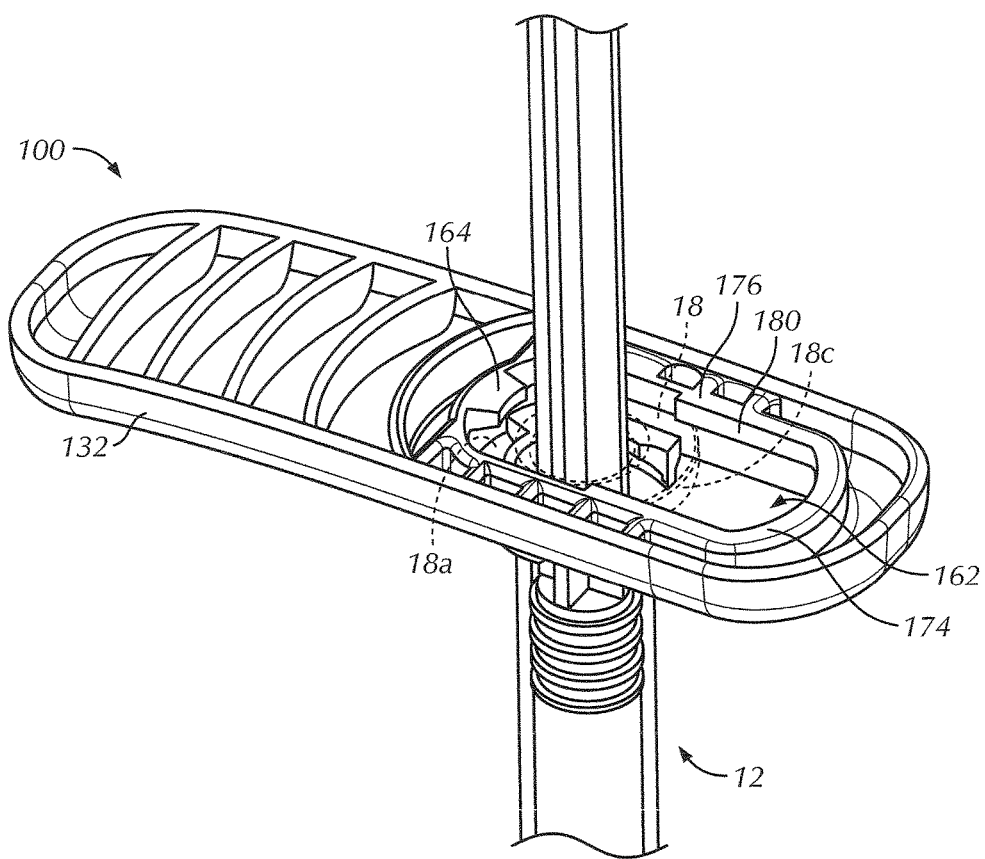
FIG. 15 is an enlarged partial top perspective view of the adapter and syringe shown in FIG. 14 from a different perspective.
Figure 16:
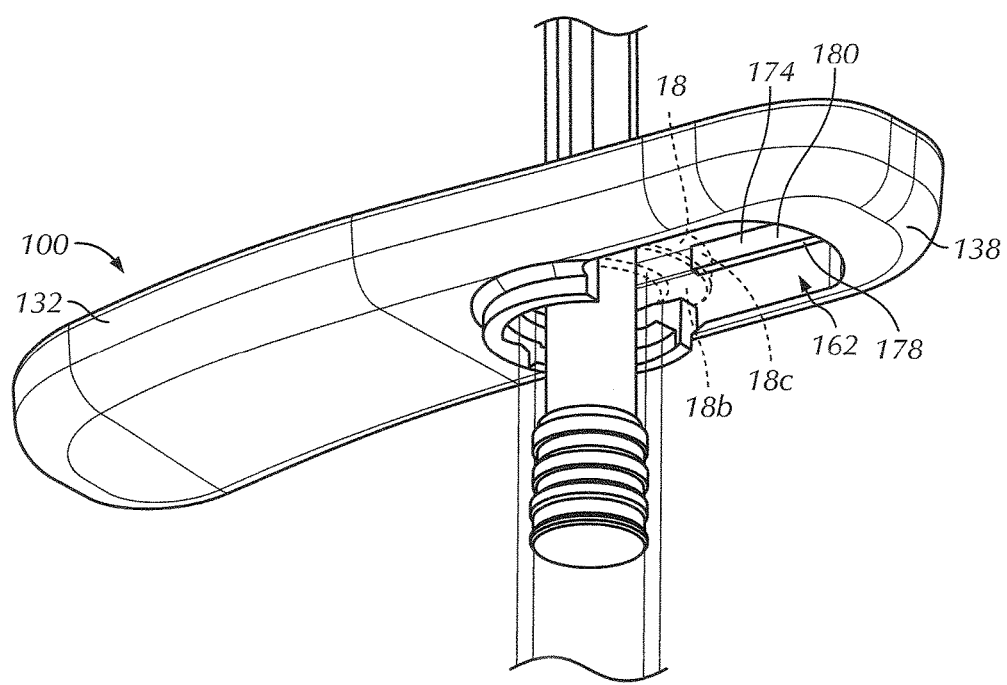
FIG. 16 is a bottom perspective view of the adapter and syringe shown in FIG. 14.

At this point, the adapter 100 and the syringe 12 are preferably moved laterally (linearly) with respect to one another to a locked or secured position (see FIGS. 14-16). More specifically, the entire adapter 100 may be moved laterally (i.e., perpendicular to the longitudinal axis A of the syringe 12 or parallel to the longitudinal axis F' of the adapter 100) until at least a portion of the flange 18 of the syringe 12 is positioned between the bottom surface 168 of the projection 164 and the top surface 124 of the base portion 120. Alternatively or additionally, the entire adapter 100 is preferably moved laterally (i.e., perpendicular to the longitudinal axis A of the syringe 10 or parallel to the longitudinal axis F' of the adapter 100) until the two tabs 131 engage at least a portion of the barrel 14 of the syringe 12.

In the locked or secured position (see FIGS. 14-16), at least a portion of the top surface 18a of the flange 18 of the syringe 12 preferably contacts at least a portion of the bottom surface 168 of the projection 164 of the adapter 100. Further, in the locked or secured position (see FIGS. 14-16), at least a portion of an outer periphery of the bottom surface 18b of the flange 18 of the syringe 12 contacts at least a portion of the top surface 124 of the base portion 120 and/or covers or is vertically aligned with the aperture 172. In other words, at least a portion of the flange 18 of the syringe 12 can become sandwiched or captured between the projection 164 and the base portion 120 of the adapter 100. Moreover, in the locked or secured position (see FIGS. 14-16), at least a portion of each of the tabs 131 engages or contacts at least a portion of an exterior of the barrel 14 of the syringe 12. It is preferred that the combination of the above engagement or connections allows the adapter 100 to be secured, attached or locked onto the syringe 12.

A method of attaching the adapter 100 of the second preferred embodiment to the syringe 12 of the present invention preferably includes generally aligning the longitudinal axis A of the syringe 12 with the geometric center of the sliding hole 162 of the adapter. The method preferably includes inserting a proximal end of the syringe 12 upwardly into the sliding hole 162 of the adapter 100. It is preferred that the adapter 100 is moved with respect to the syringe 12 along the longitudinal axis A thereof or slid along the barrel 14 toward the flange 18 of the syringe 12 until the top surface 124 of the base portion 120 is at least generally coplanar with the bottom surface 18b of the flange 18. It is preferred that the adapter 100 is then moved laterally (i.e., parallel to the longitudinal axis F' of the adapter 100) with respect to the syringe 12 to generally fix or lock the adapter 100 onto the flange 18 of the syringe 12. It is preferred that an audible or tactile sound or click is generated once the flange 18 is positioned with respect to the adapter 100 as shown in FIGS. 14-16, so as to alert the user that the adapter 100 is in a final locked configuration. The audible or tactile sound or click may be generated by at least one of the tabs 131 contacting the barrel 14 of the syringe 12 and/or at least a portion of the flange 18 of the syringe 12 being captured between the projection 164 and the base portion 120 of the adapter 100. Once the adapter 100 is in the locked or secured position (see FIGS. 14-16), the syringe 12 may be used as is conventional in the art.

It will be understood by those skilled in the art that each of the adapters 10, 100 may be designed to be permanently locked onto the syringe 12 once the adapter 10, 100 is in the final locked configuration. In such an embodiment, the adapter 10, 100 is preferably discarded along with the used syringe 12 after use. In an alternative embodiment, the adapter 10, 100 may be removable from the syringe 12 after the adapter 10, 100 is placed in the final locked or secured configuration.

In the first preferred embodiment, the adapter 10 is removed from the syringe 12 by rotating the adapter in an opposing second rotational direction (i.e., counterclockwise) to remove portions of the flange 18 from between the projection(s) 46 and the ramp portion(s) 52, and then sliding or moving the adapter 10 off of the syringe 12. In the second preferred embodiment, the adapter 100 is preferably removed from the syringe 12 by sliding the adapter 100 laterally (i.e., parallel to the longitudinal axis F' of the adapter 100) such that the syringe 12 moves from within the insertion hole 122 to within the sliding hole 162 of the adapter 100. Then, it is preferred that the syringe 12 is moved along the longitudinal axis A thereof until the entire syringe 12 has been removed from the sliding hole 162 of the adapter 100. In both embodiments, the adapter 10, 100 would be reusable and able to be used with a plurality of different syringes 12.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An adapter for a syringe comprising:
a base portion having an insertion hole configured to surround and engage at least a portion of a barrel of the syringe, the base portion including a top surface and an opposing bottom surface, at least one projection extending upwardly from the top surface of the base portion, at least one ramp portion located proximate the at least one projection; and a flange portion extending laterally outwardly from the base portion, the flange portion including a top surface and an opposing bottom surface, the top surface of the base portion extending generally parallel to and spaced between the top surface and the bottom surface of the flange portion, wherein the adapter is configured to be locked onto the barrel of the syringe by sliding the adapter along the barrel until the top surface of the base portion of the adapter contacts a bottom surface of a flange of the syringe and then rotating the adapter in a first rotational direction with respect to the syringe until the flange is positioned between a bottom surface of the at least one ramp portion and the top surface of the base portion.

2. The adapter according to claim 1, wherein the flange portion has a longitudinal axis extending from a first distal end thereof to an opposing second distal end thereof, a first distance measured from a geometric center of the insertion hole to the first distal end of the flange portion being less than a second distance measured from the geometric center of the insertion hole to the second distal end of the flange portion.

3. The adapter according to claim 1, wherein the top surface and the bottom surface of the flange portion have nonlinear cross-sectional shapes.

4. The adapter according to claim 1, wherein a peripheral edge of the bottom surface of the flange portion is concave.

5. The adapter according to claim 1, wherein the at least one projection and the at least one ramp portion are configured to hold the flange of the syringe in place when the adapter is locked onto the barrel of the syringe.

6. The adapter according to claim 5, wherein the flange of the syringe is configured to be rotated between the at least one projection and the at least one ramp portion.

7. An adapter for a syringe comprising:
a base portion having an insertion hole configured to surround and engage at least a portion of a barrel of the syringe, the base portion including a top surface and an opposing bottom surface, at least one projection extending upwardly from the top surface of the base portion, at least one ramp portion located proximate the at least one projection; and
a flange portion extending laterally outwardly from the base portion, the flange portion including a top surface and an opposing bottom surface, the top surface of the base portion extending generally parallel to and spaced between the top surface and the bottom surface of the flange portion,
wherein the top surface of the flange portion includes at least one rib that extends generally perpendicularly to a longitudinal axis of the flange portion which extends from a first distal end thereof to an opposing second distal end thereof.

8. The adapter according to claim 7, wherein the adapter is configured to be locked onto the barrel of the syringe h sliding the adapter along the barrel and then rotating the adapter in a first rotational direction with respect to the syringe.

9. The adapter according to claim 7, wherein the at least one projection and the at least one ramp portion are configured to hold a flange of the syringe in place when the adapter is locked onto the barrel of the syringe.

10. The adapter according to claim 7, wherein when the adapter is locked onto the barrel of the syringe, at least a portion of a flange of the syringe is positioned between the at least one ramp portion and the top surface of the base portion.

11. The adapter according to claim 7, wherein a top surface of the at least one ramp portion is generally coplanar with the top surface of the flange portion and at least a portion of a bottom surface of the at least one ramp portion extends at an angle of approximately 5-45 degrees with respect to a plane defined by the top surface of the at least one ramp portion.

12. The adapter according to claim 5, wherein the at least one projection includes two spaced-apart projections extending upwardly from the top surface of the base portion and the at least one ramp portion includes two spaced-apart ramp portions, and a flange of the syringe is configured to be rotated between and held in place by the two spaced-apart projections and the two spaced-apart ramp portions.

13. An adapter for a syringe comprising:
a base portion having an insertion hole configured to surround and engage at least a portion of a barrel of the syringe, the base portion including a top surface and an opposing bottom surface, at least one projection extending upwardly from the top surface of the base portion, at least one ramp portion located proximate the at least one projection; and
a flange portion extending laterally outwardly from the base portion, the flange portion including a top surface and an opposing bottom surface, the top surface of the base portion extending generally parallel to and spaced between the top surface and the bottom surface of the flange portion,
wherein a top surface of the at least one ramp portion is generally coplanar with the top surface of the flange portion and at least a portion of a bottom surface of the at least one ramp portion extends at an angle of approximately 5-45 degrees with respect to a plane defined by the top surface of the at least one ramp portion.

14. The adapter according to claim 13, wherein the adapter is configured to be locked onto the barrel of the syringe by sliding the adapter along the barrel and then rotating the adapter in a first rotational direction with respect to the syringe.

15. The adapter according to claim 13, wherein the at least one projection and the at least one ramp portion are configured to hold a flange of the syringe in place when the adapter is locked onto the barrel of the syringe.

16. The adapter according to claim 10, wherein the at least one projection includes two spaced-apart projections extending upwardly from the top surface of the base portion and the at least one ramp portion includes two spaced-apart ramp portions, and a flange of the syringe is configured to be rotated between and held in place by the two spaced-apart projections and the two spaced-apart ramp portions.

17. An adapter for a syringe comprising:
a base portion having an insertion hole configured to surround and engage at least a portion of a barrel of the syringe, the base portion including a top surface and an opposing bottom surface, at least one projection extending upwardly from the top surface of the base portion, at least one ramp portion located proximate the at least one projection; and
a flange portion extending laterally outwardly from the base portion, the flange portion including a top surface and an opposing bottom surface, the top surface of the base portion extending generally parallel to and spaced between the top surface and the bottom surface of the flange portion,
wherein the at least one projection includes two spaced-apart projections extending upwardly from the top surface of the base portion and the at least one ramp portion includes two spaced-apart ramp portions, and a flange of the syringe is configured to be rotated between and held in place by the two spaced-apart projections and the two spaced-apart ramp portions.

18. The adapter according to claim 17, wherein the adapter is configured to be locked onto the barrel of the syringe by sliding the adapter along the barrel and then rotating the adapter in a first rotational direction with respect to the syringe.

19. The adapter according to claim 17, wherein the at least one projection and the at least one ramp portion are configured to hold a flange of the syringe in place when the adapter is locked onto the barrel of the syringe.

* * * * *

UNITED STATES PATENT AND TRADEMARK OFFICE
CERTIFICATE OF CORRECTION

PATENT NO. : 10,398,841 B2  
APPLICATION NO. : 15/651414  
DATED : September 3, 2019  
INVENTOR(S) : Christopher Evans et al.

Page 1 of 1

It is certified that error appears in the above-identified patent and that said Letters Patent is hereby corrected as shown below:

In the Claims

Column 11, Claim number 8, Line number 52, should read:
The adapter according to claim 7, wherein the adapter is configured to be locked onto the barrel of the syringe by sliding the adapter along the barrel and then rotating the adapter in a first rotational direction with respect to the syringe.

Column 12, Claim number 12, Line number 5, should read:
The adapter according to claim 7, wherein the at least one projection includes two spaced-apart projections extending upwardly from the top surface of the base portion and the at least one ramp portion includes two spaced-apart ramp portions, and a flange of the syringe is configured to be rotated between and held in place by the two spaced-apart projections and the two spaced-apart ramp portions.

Column 12, Claim number 16, Line number 42, should read:
The adapter according to claim 13, wherein the at least one projection includes two spaced-apart projections extending upwardly from the top surface of the base portion and the at least one ramp portion includes two spaced-apart ramp portions, and a flange of the syringe is configured to be rotated between and held in place by the two spaced-apart projections and the two spaced-apart ramp portions.

Signed and Sealed this  
Twenty-first Day of January, 2020

Andrei Iancu  
*Director of the United States Patent and Trademark Office*